US009572241B1

(12) United States Patent
Eckert et al.

(10) Patent No.: US 9,572,241 B1
(45) Date of Patent: Feb. 14, 2017

(54) DEVICES FOR CREATING NON-THERMAL PLASMA AND OZONE

(71) Applicant: ChiScan Holdings, LLC, Las Vegas, NV (US)

(72) Inventors: Bradley N Eckert, Chandler, AZ (US); Huan Truong, Chandler, AZ (US); Bryon K Eckert, Chandler, AZ (US)

(73) Assignee: ChiScan Holdings, LLC, Las Vegas, NV (US)

(*) Notice: Subject to any disclaimer, the term of this patent is extended or adjusted under 35 U.S.C. 154(b) by 0 days.

(21) Appl. No.: 15/055,028

(22) Filed: Feb. 26, 2016

Related U.S. Application Data

(60) Provisional application No. 62/235,517, filed on Sep. 30, 2015.

(51) Int. Cl.

| | |
|---|---|
| ***H01J 17/26*** | (2012.01) |
| ***H05H 1/24*** | (2006.01) |
| *A61F 11/00* | (2006.01) |
| *A61N 5/00* | (2006.01) |

(52) U.S. Cl.
CPC ............. *H05H 1/2406* (2013.01); *A61F 11/00* (2013.01); *A61N 5/00* (2013.01); *H05H 2001/2412* (2013.01); *H05H 2001/2425* (2013.01)

(58) Field of Classification Search
CPC ............................ A61B 18/042; H05H 1/2406
See application file for complete search history.

(56) References Cited

U.S. PATENT DOCUMENTS

| | | | | |
|---|---|---|---|---|
| 6,284,983 | B1 * | 9/2001 | Lutschounig | H05K 1/16 174/260 |
| 7,280,874 | B2 | 10/2007 | Boehm | |
| 2010/0145253 | A1 * | 6/2010 | Gutsol | A61B 18/042 604/20 |
| 2012/0259270 | A1 * | 10/2012 | Wandke | A61N 1/0408 604/23 |
| 2013/0038199 | A1 * | 2/2013 | Roy | H05H 1/24 313/231.31 |
| 2013/0345620 | A1 * | 12/2013 | Zemel | A61B 18/042 604/24 |

(Continued)

OTHER PUBLICATIONS

Alekseev, Oleg et al., Nonthermal Dielectric Barrier Discharge (DBD) Plasma Suppresses Herpes Simplex Virus Type 1 (HSV-1) Replication in Corneal Epithelium, TVST, 2014, pp. 1-14, vol. 3, No. 2.

(Continued)

*Primary Examiner* — Joseph L Williams

(57) ABSTRACT

A plurality of non-thermal plasma emitters is disposed on a rigid or flexible substrate. The rigid substrate enables the device to be pre-formed in any shape and the flexible substrate enables the device to conform to any surface topography at the time of treatment. The substrate is a dielectric material and in a preferred embodiment is made of thin FR-4. Each of the plasma emitters has a drive electrode on one side of the substrate and a ground electrode on the opposing side of the substrate. In the preferred embodiment both electrodes are centered over a through-hole in the substrate. A conductive drive track is connected to each drive electrode and a conductive ground track is connected to each ground electrode. A drive terminal is connected to the drive track and a ground terminal is connected to the ground track.

20 Claims, 9 Drawing Sheets

(56) References Cited

U.S. PATENT DOCUMENTS

2014/0217882 A1* 8/2014 Yagi .................... H05H 1/2406 313/268

OTHER PUBLICATIONS

Algwari, Q.T. et al., Cold plasma jet developed that could kill superbugs, PLoS One, 2012, vol. 7, No. 8.
Arora, V. et al., Cold Atmospheric Plasma (CAP) in Dentistry, Dentisty, 2014, pp. 1-5, vol. 4, No. 1.
Barekzi, Nazir, Dose-dependent killing of leukemia cells by low-temperature plasma, Journal of Physics D Applied Physics, 2012, pp. 1-6, vol. 45.
Boonyawan, Dheerawan, Non-Thermal Plasma for Acne and Aesthetic Skin Improvement, Plasma Medicine, Jan. 2014, pp. 79-88, vol. 4. No. 1-4.
Boxhammer, V. et al., Investigation of the mutagenic potential of cold atmospheric plasma at bactericidal dosages, Mutation Research/Fundamental and Molecular Mechanisms of Mutagenesis.
Byrne, Christopher et al., The ingestible telemetric body core temperature sensor: a review of validity and exercise applications, Sports Med, 2007, pp. 126-133, vol. 41.
Cahill, Orla et al., Cold Air Plasma to Decontaminate Inanimate Surfaces of the Hospital Environment, American Society for Microbiology, 2014, pp. 1-29.
Cahill, Orla et al., Cold Air Plasma to Decontaminate Inanimate Surfaces of the Hospital Environment, Applied and Environmental Microbiology, Mar. 2014, pp. 2004-2011, vol. 80, No. 6.
Cheng, Xiaoqian et al., The Effect of Tuning Cold Plasma Composition on Glioblastoma Cell Viability, PoLS One, 2014, pp. 1-9, vol. 9, No. 5.
Crozes, Gill et al., Synergies of UV Disinfection and Ozone in Water Treatment, International UV Association, 2003, pp. 1-5, Vienna, Austria.
Daeschlein, Georg et al., Plasma meets Dermatology: Clinical aspects in preventive and curative Medicine, German Federal Ministry of Education and Research (grant No. 13N9773 and 13N9779).
Dobrynin, Danil et al., Fast Blood Coagulation of Capillary Vessels by Cold Plasma: A Rat Ear Bleeding Model, Plasma Medicine, 2011, pp. 241-247, vol. 1, Philadelphia, Pennsylvania.
Dobrynin, Danil et al., Physical and biological mechnaisms of direct plasma interaction with living tissue, Institute of Physics, New Journal of Physics, 2009, pp. 1-26, vol. 11.
Dowling, Denis, Plasma medicine—new technology for anti-ageing and wound healing, Applied and Enviromental Microbiology, 2013.
Erfurt-Berge, Cornelia et, Recent Developments in Topical Wound Therapy: Impact of Antimicrobiological Changes and Rebalancing the Wound Milieu, BioMed Research International, 2014, pp. 1-8.
Ferrell, James et al., Characterization, Properties and Applications of Nonthermal Plasma: A Novel Pulsed-Based Option, Biotechnol Biomater, 2013, pp. 1-10, vol. 3, No. 2.
Fridman, Alexander et al., Plasma Medicine, book published in 2013, Chapters 1-4, 6-10, Wiley Publishing.
Fridman, Gregory et al., Floating Electrode Dielectric Barrier Discharge Plasma in Air Promoting Apoptotic Behavior in Melanoma Skin Cancer Cell Lines, Drexel University College of Engineering.
Fulton, Judith, Sterilization of Infected Wounds with Non-thermal Plasma, Akron General Medical Center, Presented at: Consortium for Wound Healing Research and Education.
Graves, David, Low temperature plasma biomedicine: A tutorial review, Physics of Plasmas, 2014, pp. 1-12, vol. 21.
Guceri, Selcuk et al., Plasma Assisted Decontamination at Biological and Chemical Agents, NATO Science for Peace and Security Series A: Chemistry and Biology.
Gupta, Aditya et al., Device-based Therapies for Onychomycosis Treatment, Skin Therapy Letter, 2012, vol. 17, No. 9.
Haertel, Beate et al., Non-Thermal Atmospheric-Pressure Plasma Possible Application in Wound Healing, Biomolecules and Therapeutics, The Korean Society of Applied Pharmacology, 2014, pp. 477-490.
Hameroff, Stuart, Ultimate Computing, Biomolecular Consciousness and NanoTechnology, Elsevier Science Publishers, Tucson, AZ.
Heinlin, Julia et al., Plasma medicine: possible applications in dermatology, The Authors Journal compilation Blackwell Verlag GmbH, 2010, pp. 1-9.
Hensel, Karol et al., Plasma for bio-decontamination, medicine and food security, NATO Advanced Research Workshop, 2011, Presented in Jasna, Slovakia.
Hermann, Hans et al., Chemical Warfare Agent Decontamination Studies in the Plasma Decon Chamber, IEEE Transactions on Plasma Science, 2002, pp. 1460-1471, vol. 30, No. 4.
Hirst, A.M. et al., Low-temperature plasma treatment induces DNA damage leading to necrotic cell death in primary prostate epithelial cells, British Journal of Cancer, 2015, pp. 1536-1545, vol. 112.
Hirst, A.M. et al., Low-temperature plasma treatment induces DNA damage leading to necrotic cell death in primary prostate epithelial cells, British Journal of Cancer, 2015, pp. 1536-1545.
Hoffmann, Clotilde et al., Cold Atmospheric Plasma: methods of production and application in dentistry and oncology, Medical Gas Research, 2013, pp. 1-15 vol. 3, No. 21.
Isbary, G., Cold atmospheric argon plasma significantly decreases bacterial load of chronic infected wounds in patients, Klinkum Schwabing.
Isbary, G. et al., Cold atmospheric plasma devices for medical issues, Expert Review of Medical Devices, 2013, pp. 376-377, vol. 10, No. 3.
Isbary, G. et al., Cold atmospheric plasma: A successful treatment of lesions in Hailey-Hailey disease, Archives of Dermatology, 2011, pp. 368-390, vol. 147, No. 4.
Isbary, G. et al., Non-thermal plasma—More than five years of clinical experience, Clinical Plasma Medicine, 2013, pp. 19-23, vol. 1.
Jeong-Hae, Choi et al., Low-temperature atmospheric plasma increases the expression of anti-aging genes of skin cells without causing cellular damages, Original Paper, Springer, 2012, pp. 1-8.
Jhang, Hogun, Effects of radio frequency waves on di ssipative low frequency instabilities in mirror plasmas, 32nd EPS Conference on Plasma Phys. Tarragona, Jun. 27-Jul. 1, 2005 ECA vol. 29C, P-1.055.
Jiang, Weiman et al., Characterization of argon direct-current glow discharge with a longitudinal electric field applied at ambient air, Scientific Reports, 2014, pp. 1-6, vol. 4, No. 6323.
Joerres, Kyle, Characterization of Cold Atmospheric Plasma, Milwaukee School of Engineering, National Science Foundation Grant, Jun. 1-Aug. 8, 2014.
Joh, Hea Min, Effect of additive oxygen gas on cellular response of lung cancer cells induced by atmospheric pressure helium plasma jet, Scientific Reports, 2014, pp. 1-9, vol. 4, No. 6638.
Kalghatgi, S. et al., Transdermal drug delivery using cold plasmas, 22nd International Symposium on Plasma Chemistry Jul. 5-10, 2015; Antwerp, Belgium.
Karol Hensel and Zdenko Machala Editors, Book of Abstracts: NATO Science Advanced Research Workshop on Plasma for bio-decontamination, medicine and food security, Mar. 15-18, 2011, Jasná, Slovakia.
Klampfl, Toblas, Cold Atmospheric Air Plasma Sterilization against Spores and Other Microorganisms of Clinical Interest, Applied and Environmental Microbiology, 2012, pp. 5077-5082, vol. 78, No. 15.
Korachi, May et al., Low temperature atmospheric plasma for microbial decontamination, FORMATEX, 2013, pp. 453-459.
Kowalski, W.J. et al., Bactericidal Effects of High Airborne Ozone Concentrations on *Escherichia coli* and *Staphylococcus aureus*, Ozone Science and Engineering, 1998, pp. 205-221, vol. 20.
Kvam, Erik et al., Nonthermal Atmospheric Plasma Rapidly Disinfects Multidrug-Resistant Microbes by Inducing Cell Surface Damage, Antimicrobial Agents and Chemotherapy, 2012, pp. 2028-2036, vol. 56, No. 4.

(56) References Cited

OTHER PUBLICATIONS

Laroussi, Mounir, Plasma Medicine: Low Tempera Pure Plasma as a Transformational Technology for the Healthcare Field, Laser & Plasma Engineering Institute Old Dominion University, 2012.
Laroussi, Mounir, Plasma-Based Sterilization, Electrical & Computer Engineering Department Old Dominion University, pp. 11-12.
Laroussi, Mounir, Temperature Plasmas for Medicine?, IEEE Transactions on Plasma Science, 2009, pp. 714-725, vol. 37, No. 6.
Li, Yang-Fang, Optimizing the distance for bacterial treatment using surface micro-discharge plasma, New Journal of Physics, 2012, pp. 1-11, vol. 14.
Liang, Yongdong et al., Rapid Inactivation of Biological Species in the Air using Atmospheric Pressure Nonthermal Plasma, American Chemical Society, 2012, pp. A-I.
Maslennikov, Oleg et al., Ozone Therapy in Practice, Health Manual, Ministry of Health Service of the Russian Federation the State Medical Academy of Nizhny Novgorod, 2008, pp. 1-48, Russia.
McDonnell, Kevin et al., Evaluation of the sensitivity of bacterial and yeast cells to cold atmospheric plasma jet treatments, Biointerphases, 2015, pp. 1-9, vol. 10, No. 2.
McTaggart, Lynne, The Quest for the Secret Force of the Universe, Harper Collins Publishers, 2001, pp. 1-289.
Metelmann, Hans-Robert, Head and neck cancer treatment and physical plasma, Clinical Plasma Medicine, 2015, pp. 17-23, vol. 3.
Mikikian, M. et al., Book of Abstracts, 4th International Conference on Plasma Medicine, 2012, Presented in Orleans France.
Misra, N.N. et al., Applications of cold plasma technology in food packaging, Trends in Food Science and Technology, Jan. 2014, pp. 5-17, vol. 35.
Mogul, Rakesh et al., Biomolecular Effects of Cold Plasma Exposure, Astrobiology Technolgy Branch, NASA.
Navya Mastanaiah, Effect of Dielectric and Liquid on Plasma Sterilization Using Dielectric Barrier Discharge Plasma.
Absolute Ozone, Certification of Ozone in USA Food Industries, Fact Sheet on the Guidelines for Limiting Exposure to Electric Fields Induced by Movement of the Human Body in a Static Magnetic Field and by Time-Varying Magnetic Fields, Health.
Laser Partners of Oklahoma, Fungi-X.
WHO, Health care-associated infections Fact Sheet, World Health Organization.
ICNIRP, ICNIRP Guidelines for Limiting Exposure to Electric Fields Induced by Movement of the Human Body in a Static Magnetic Field and by Time-Varying Magnetic Fields Below 1 Hz, Health.
LifeVantage, LifeVantage TrueScience with enchanced Nrf2 technologies Presentation, Ozone Conversion Units, Physical Properties, Standard conditions.
EPA, Ozone, EPA Guidance Manual Alternative Disinfectants and Oxidants, Apr. 1999, pp. 1-52, vol. 3, No. 1.
Max Planck Institute, Plasma Health Care, A project initiated by the Max Planck Institute for Extraterrestrial Physics.
Drexel, Plasma Medicine: Physical and Biological Mechanisms of Plasma Interaction with Living Tissue Presentation.
Max Planck Institute, Plasma Medicine: Sterilisation and Improved Wound Healing, Max-Planck-Innovation Presentation.
Max Planck Institute, Terraplasma GmbH Flyer, Max Planck Society.
Electroherbalism, The Consolidated Annotated Frequency List (CAFL), The Electroherbalism Frequency Lists, Third Edition, www.electroherbalism.com, Typical Dosage and Reaction Times to kill bacteria with Ozone.
BC Hydro, Understanding Electric and Magnetic Fields, BC Hydro.
Oryan, Ahmad et al., Bone regenerative medicine: classic options, novel strategies, and future directions, Journal of Orthopaedic Surgery and Research, 2014, pp. 1-27, vol. 9, No. 18.
Palou, Lluis et al., Effects of continuous 0.3 ppm ozone exposure on decay development and physiological responses of peaches and table grapes in cold storage, Postharvest Biology and Technology, 2002.
Pan, Jie et al., A Novel Method of Tooth Whitening Using Cold Plasma Microjet Driven by Direct Current in Atmospheric-Pressure Air,Transactions on Plasma Science, 2010, pp. 3143-3151, vol. 38, No. 11.
Papana, Angeliki et al., Detecting causality in non-stationary time series using Partial Symbolic Transfer Entropy: Evidence in nancial data.
Pournaseh, Yasaman et al, Cold atmospheric plasma jet against Leishmania major in vitro study, Basic Research Journal of Medicine and Clinical Sciences, 2014, pp. 90-94, vol. 4, No. 3.
Ren, Y.X. et al., Mutation Induction by DBD Plasma in Phosphate-solubilizing Bacteria Enterobacter Agglomerans, Energy Procedia, 2012, pp. 211-216, vol. 16.
Rice, Rip et al., U.S. FDA Regulatory Approval of Ozone as an Antimicrobial Agent—What Is Allowed and What Needs to Be Understood, RICE International Consulting Enterprises, pp. 1-13.
Rosani, Umberto et al., Atmospheric-Pressure Cold Plasma Induces Transcriptional Changes in Ex Vivo Human Corneas, PLoS One, 2015, pp. 1-17.
Rutala, William et al., Guideline for Disinfection and Sterilization in Healthcare Facilities, Infection Control Practices Advisory Committee (HICPAC), 2008.
Sarghini, Fabrizio, Cold Plasma Technology: Applications in Food Industry, DIIAT—University of Naples Federico II, Italy.
Sarghini, Fabrizio, Cold PlasmaTechnology: Applications in Food Industy, DIIAT—University of Naples Federico II, Italy.
Shimizu, T et al., Atmospheric Plasma in Medicine: Chronic Wound Disinfection, Applied and Environmental Microbiology.
Shimizu, T et al., The dynamics of ozone generation and mode transition in air surface micro-discharge plasma at atmospheric pressure, New Journal of Physics, 2012, pp. 1-11, vol. 14.
Sivitz, William et al., Mitochondrial Dysfunction in Diabetes: From Molecular Mechanisms to Functional Significance and Therapeutic Opportunities, Antioxidants & Redox Signaling, 2010, pp. 537-577, vol. 12.
Sprey, Karen, Cold plasma therapy could provide an alternative to antibiotics, Dec. 21, 2010, pp. 1-2.
Sun, Peter et al., Atmospheric pressure cold plasma as an antifungal therapy, Applied Physics Letters, American Institute of Physics, 2011, pp. 1-3, vol. 98.
Svarcova, Michaela et al., Treatment of a Superficial Mycosis by Low-temperature Plasma: A Case Report, Prague Medical Report, 2014, pp. 73-78, vol. 115, No. 1.
Virard, Francois et al., Cold Atmospheric Plasma Induces a Predominantly Necrotic Cell Death via the Microenvironment, PoLS One, 2015, pp. 1-16.
Wang, Mian et al., Cold Atmospheric Plasma for Selectively Ablating Metastatic Breast Cancer Cells, PLOS One, Sep. 2013, pp. 1-11, vol. 8, No. 9.
Weiss, Martin et al., Cold Atmospheric Plasma Treatment Induces Anti-Proliferative Effects in Prostate Cancer Cells by Redox and Apoptotic Signaling Pathways, PLoS One, 2015, pp. 1-17.
Wikol, Michael et al., Expanded Polytetrafluoroethylene Membranes and Their Applications, Filtration and Purification in the Biopharmaceutical Industry, Second Edition, pp. 619-640.
Wu, Yan et al., MS2 Virus Inactivation by Atmospheric-Pressure Cold Plasma Using Different Gas Carriers and Power Levels, Applied and Environmental Microbiology, 2015, pp. 996-1002, vol. 81 No. 3.
Yoshinari, Masao et al., Surface modification by cold-plasma technique for dental implants—Bio-functionalization with binding pharmaceuticals, Japanese Dental Science Review, 2011, pp. 89-101.
Zhang, Hao, Effects and Mechanism of Atmospheric-Pressure Dielectric Barrier Discharge Cold Plasma on Lactate Dehydrogenase (LDH) Enzymet, Scientific Reports, 2015, pp. 1-12, vol. 5, No. 10031.
Zhu, Wei et al., Cold Atmospheric Plasma Modified Electrospun Scaffolds with Embedded Microspheres for Improved Cartilage Regeneration, PoLS One, 2015, pp. 1-18.
Zimmermann, Julia et al., In vivo skin treatment using two portable plasma devices: Comparison of a direct and an indirect cold atmospheric plasma treatment, Clinical Plasma Medicine, 2013, pp. 35-49, vol. 1.

* cited by examiner

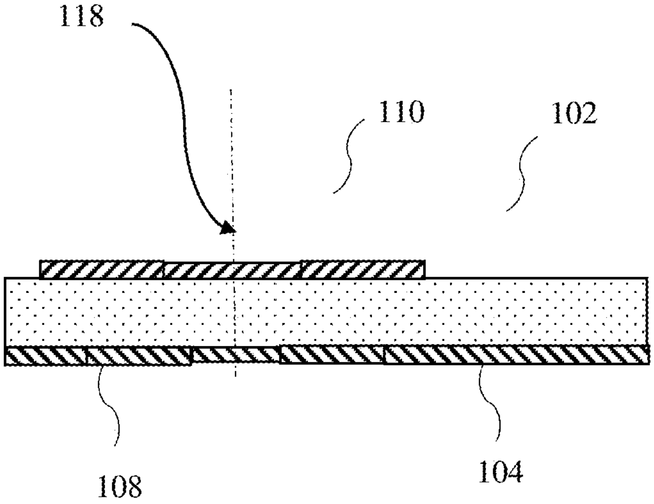
FIG. 2A
[new]

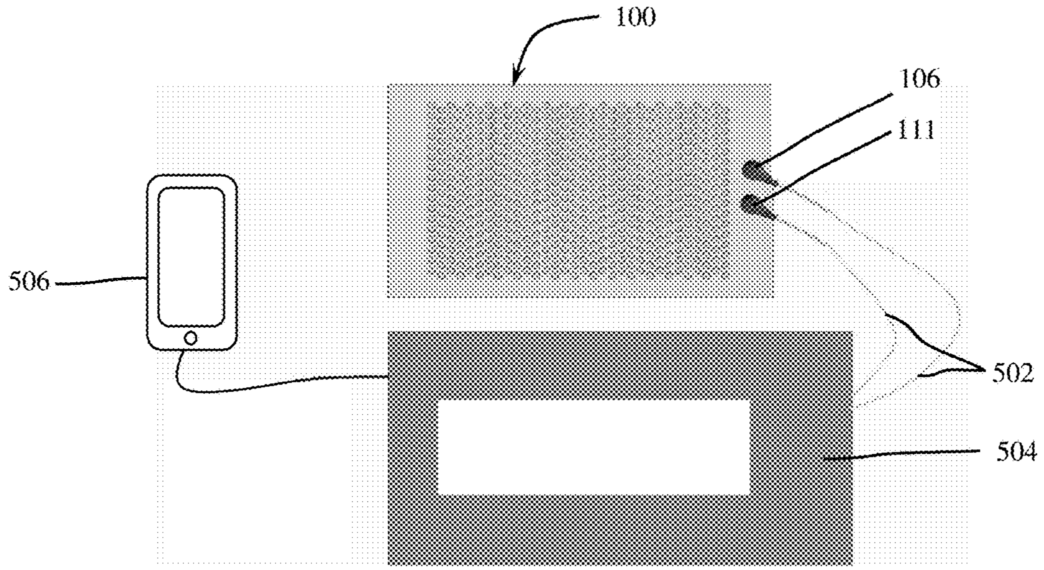
FIG. 8A
[new]

DEVICES FOR CREATING NON-THERMAL PLASMA AND OZONE

CROSS-REFERENCE TO RELATED APPLICATIONS

This application claims the benefit of U.S. Provisional Application No. 62/235,517 filed Sep. 30, 2015.

FIELD OF INVENTION

The present specification relates to devices for creating non-thermal plasma and ozone on a rigid or flexible substrate over a small or large surface area.

BACKGROUND

Plasma is an ionized state of matter known for its cleaning, decontaminating, sterilizing, antimicrobial and healing properties when applied to an inanimate surface or to tissue. Plasma can be created when energy is applied to a substance. As energy input is increased the state of matter changes from solid, to liquid, to a gaseous state. If additional energy is fed into the gaseous state, the atoms or molecules in the gas will ionize and change into the energy-rich plasma state, or the fourth fundamental state of matter.

There are two types of plasma, thermal and non-thermal, which is also known as cold plasma. Thermal plasmas are in thermal equilibrium, i.e. the electrons and the heavy particles are at the same temperature. Current technologies create thermal plasma by heating gas or subjecting the gas to a strong electromagnetic field applied with a generator. As energy is applied with heat or electromagnetic field, the number of electrons can either decrease or increase, creating positively or negatively charged particles called ions. Thermal plasma can be produced by plasma torches or in high-pressure discharges. If thermal plasma is used in treating a material or surface sensitive to heat, it can cause significant thermal desiccation, burning, scarring and other damage.

In order to mitigate such damage, methods and devices have been created for applying non-thermal plasma to heat-sensitive materials and surfaces. Whereas in thermal plasmas the heavy particles and electrons are in thermal equilibrium with each other, in non-thermal plasmas the ions and neutrals are at a much lower temperature (sometimes as low as room temperature) than the electrons. Non-thermal plasma usually can operate at less than 104° F. at the point of contact. Thus non-thermal plasmas are not likely to damage human tissue.

To create non-thermal plasma, a potential gradient is applied between two electrodes. Typically the electrodes are in an environment of a fluid such as helium, nitrogen, heliox, argon, or air. When the potential gradient is large enough between the high voltage electrode and grounded electrode, the fluid between the electrodes ionizes and becomes conductive. For example, in the plasma pencil a dielectric tube contains two disk-shaped electrodes of about the same diameter as the tube, separated by a small gap. The disks are perforated. High voltage is applied between the two electrodes and a gas mixture, such as helium and oxygen, is flowed through the holes of the electrodes. When the potential gradient is large enough, a plasma is ignited in the gap between the electrodes and a plasma plume reaching lengths up to 12 cm is discharged through the aperture of the outer electrode and into the surrounding room air. The plume can be used to treat surfaces by scanning it across the surface.

Plasma systems requiring forced gas can be very large and cumbersome, requiring the use of gas tanks to supply the necessary fluid to create the plasma. Another disadvantage is that there is only a narrow contact point between the plasma plume and the surface that it comes into contact with. Typically, plumes are usually on the order of 1 cm in diameter. This makes treating larger areas time-consuming and tedious, since the contact point has to be moved back and forth across the area to be treated. The uniformity of treatment across the treatment area may be difficult to control.

Another commonly used method for creating non-thermal plasma is the dielectric barrier discharge ("DBD"), which is the electrical discharge resulting after high voltage is applied between two electrodes separated by an insulating dielectric barrier. DBD is a practical method of generating non-thermal plasma from air at ambient temperature and comes in several variants. For example, a volume dielectric barrier discharge ("VDBD") occurs between two similar electrodes with a dielectric barrier on one electrode, and the electrodes facing each other. A VDBD is limited by the space between the two electrodes, the size of the electrodes, and cannot conform to different surface topographies. A surface dielectric barrier discharge ("SDBD") can occur between one electrode and a surface such as skin, metal, or plastic. In a specific example of SDBD, known as a floating electrode dielectric barrier discharge ("FE-DBD") variation, one of the electrodes is protected by a dielectric such as quartz and the second electrode is a human or animal skin or organ. In the FE-DBD setup, the second electrode is not grounded and remains at a floating potential. A SDBD treatment area is limited by the electrodes' size, and like the VDBD, it cannot conform to the surface the electrode comes into contact with. In current SDBD technologies there is only a single contact point between the plasma plume and the surface that it comes into contact with.

Another type of non-thermal plasma is known as corona discharge, which is an electrical discharge brought on by the ionization of a fluid surrounding a conductor that is electrically charged. Corona discharges occurs at relatively high-pressures, including atmospheric pressure, in regions of sharply non-uniform electric fields. The field near one or both electrodes must be stronger than the rest of the fluid. This occurs at sharp points, edges or small diameter wires. The corona occurs when the potential gradient of the electric field around the conductor is high enough to form a conductive region in the fluid, but not high enough to cause electrical breakdown or arcing to nearby objects. The ionized gas of a corona is chemically active. In air, this generates gases such as ozone (O3) and nitric oxide (NO), and in turn nitric dioxide (NO2). Ozone is intentionally created this way in an ozone generator, but otherwise these highly corrosive substances are typically objectionable because they are highly reactive. It would be desirable to take advantage of the reactive nature of these gas molecules.

Thus there is a need for a non-thermal plasma source that can cover larger surface areas and can conform onto or around any surface topography. There is also a need for a portable non-thermal plasma source that does not require the use of pressurized gas or accompanying gas cylinders. There is a need for a non-thermal plasma source that makes good use of reactive species created by non-thermal plasma.

SUMMARY

This device is a plurality of non-thermal plasma emitters disposed on a rigid or flexible substrate. The rigid substrate enables the device to be pre-formed in any shape and the flexible substrate enables the device to conform to or around any surface topography at the time of treatment. The substrate is made of a dielectric material and in a preferred embodiment is made of thin FR-4.

Each of the plasma emitters comprises a drive electrode on one side of the substrate and a ground electrode on the opposing side of the substrate. In the preferred embodiment both electrodes are centered over a through-hole in the substrate. A conductive drive track is connected to each drive electrode and a conductive ground track is connected to each ground electrode. A drive terminal is connected to the drive track and a ground terminal is connected to the ground track. In one embodiment the plasma emitters are arranged in rows that are offset vertically from the previous row. When an AC voltage is applied to a drive terminal, the drive electrodes are capacitively coupled to the ground electrodes and a plasma is discharged.

BRIEF DESCRIPTION OF DRAWINGS

FIG. 8A illustrates a general overview of a non-thermal plasma device with a controller and a cell phone power supply.

DETAILED DESCRIPTION

This device comprises a plurality of non-thermal plasma emitters, disposed on a rigid or flexible substrate. The emitters are arranged in an array such that when the array is connected to a voltage source the emitters generate a plurality of corona discharges. The discharges generate ionized gas, which in turn creates reactive species including ozone and nitric oxide.

Figure 1:
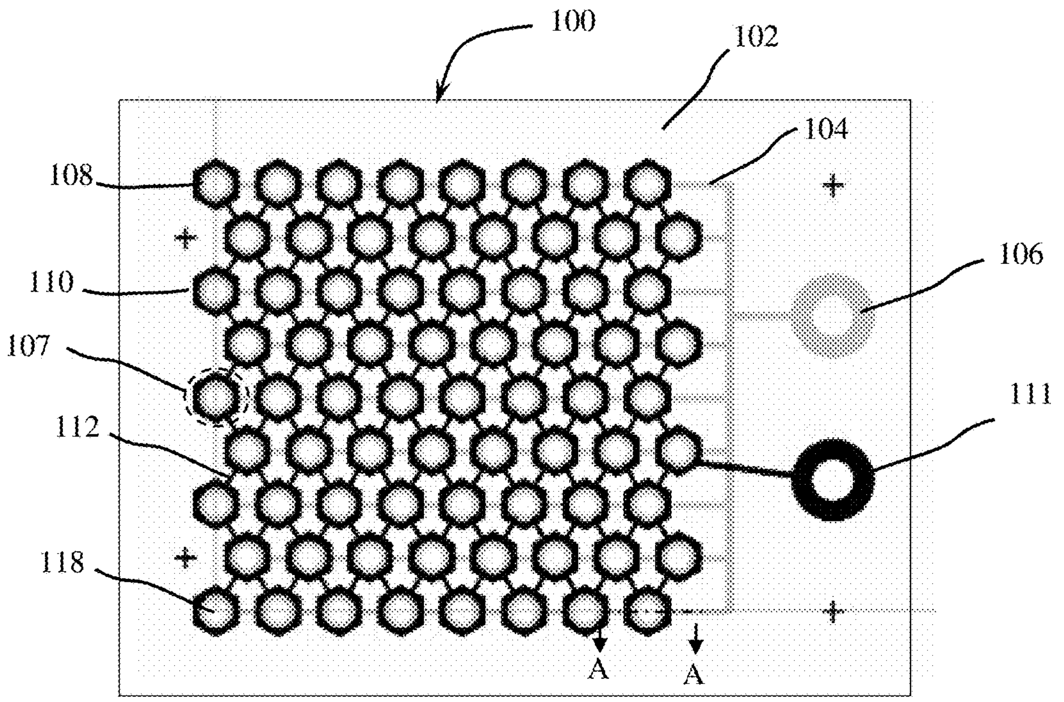
FIG. 1 is a top view of a first embodiment of a non-thermal plasma device of the present invention.
Figure 2:
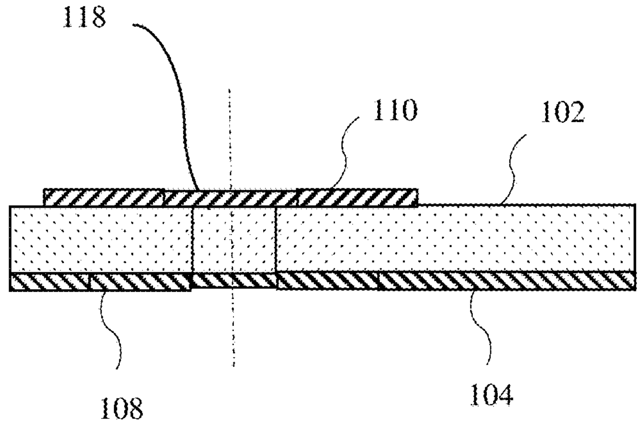
FIG. 2 is a cross-sectional view of the device along line A-A of FIG. 1.
Figure 3:
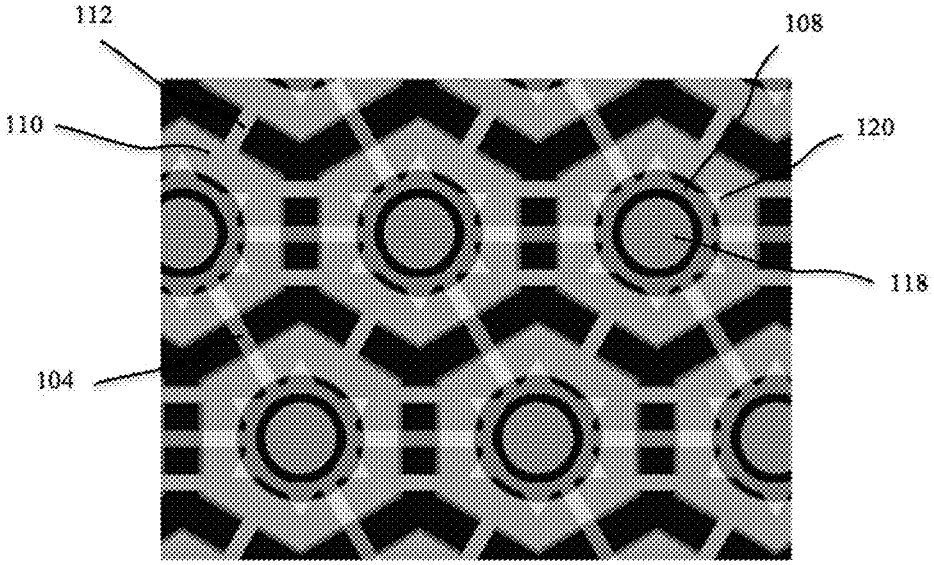
FIG. 3 is a partial top view of a second embodiment of a non-thermal plasma device.

Referring initially to FIG. 1, a non-thermal plasma device is shown generally at 100. The device comprises a substrate 102 having at least two opposing surfaces, referred to herein sometimes as a top and bottom for convenience. A plurality of through-holes 118 is made in the substrate 102. A plurality of drive electrodes 110 is placed on the top of the substrate 102, with each drive electrode 110 centered over one through-hole 118 in the substrate 102. A plurality of ground electrodes 108 is placed on the bottom of the substrate 102, with each ground electrode 108 centered over one through-hole 118 in the substrate 102. The resulting structure of a through-hole, a ground electrode, and a drive electrode comprises a plasma emitter 107. FIG. 2 shows a cross-sectional view of a plasma emitter with through-holes. Each drive electrode 110 and ground electrode 108 is generally centered on a through-hole 118, but in certain embodiments it may be off-center. Each electrode's 110 shape is preferably symmetric around the through-hole 118, such as a hexagon, circle, triangle, rectangle, square, or other shape, but in certain embodiments can be asymmetric. FIGS. 1 and 3 illustrate an embodiment in which the drive electrode 110 is hexagonal.

Figure 4:
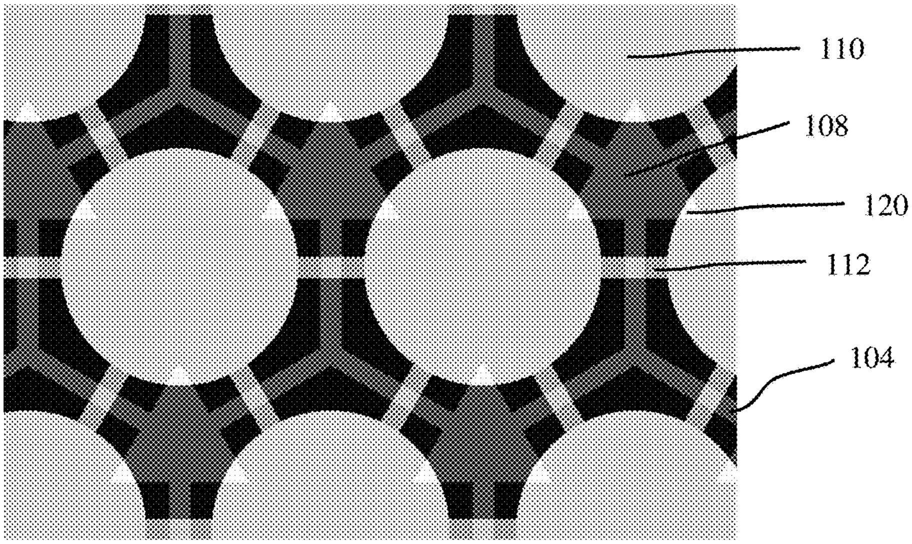
FIG. 4 is a partial top view of a third embodiment of a non-thermal plasma device without through-holes in the substrate.

FIG. 4 shows another embodiment of a non-thermal and ozone plasma device 200 wherein a substrate does not have through-holes. Here a plurality of drive electrodes 110 is placed on the top of the substrate 102, with each drive electrode 110 centered over a ground electrode 108 on the bottom of the substrate 102. The resulting structure of a drive electrode on a dielectric substrate over a ground electrode is also referred to herein as a plasma emitter 107.

A conductive drive track 112 on the top of the substrate 102 is connected to at least one drive electrode 110. A conductive ground track 104 on the bottom of the substrate 102 is connected to at least one ground electrode 108. One or more drive tracks 112 may be used to interconnect as many drive electrodes 110 together as desired. Similarly, one or more ground tracks 104 may be used to interconnect as many ground electrodes 108 together as desired. Emitters may be connected in series or in parallel, and preferably in parallel for a lower driving voltage.

A drive terminal 111 is connected to the drive track 112 and a ground terminal 106 is connected to the ground track 104. The drive electrodes 110 are interconnected and connected to a drive terminal 111. Similarly, the ground electrodes are interconnected and connected to a ground terminal 106. The resultant structure is much like a printed circuit board.

The substrate 102 is made of a dielectric material such as alumina, polycarbonate, polyimide, polyester, polytetrafluoroethylene-infused woven glass cloth, polypropylene, glass-reinforced epoxy laminate sheets, or the like. In certain embodiments a substrate has more than one layer, and the layers may be made of different materials. The substrate 102 is made of a rigid or a flexible material that can be made to conform to varying surface topography and shapes such as a rough surface, a textured surface, a smooth surface. The substrate can be two-dimensional, such as a square, curved, rectangular, round, or hexagonal. It can also be three-dimensional such as curved, cubic, tubular, or spherical.

The substrate may also have a non-uniform shape or a non-symmetric shape. Substrates of rigid materials may be shaped to the desired conformation before or after the plasma emitters are made therein. Substrates of flexible materials are typically conformed to the desired shape after the device is manufactured.

In a preferred embodiment, the substrate is made of thin FR-4. At a thickness of about 0.2 mm, the substrate made of FR-4 is somewhat flexible. As an alternative, the array can be fabricated from more flexible material such as polyimide film or PTFE infused fiberglass.

Using mass manufacturing techniques, the cost of making the arrays is small enough that the devices can be considered consumable or disposable, simply thrown away or recycled after one or a few uses. Any polymer in the array is consumed by the oxygen plasma, in a process commonly known as ashing. This erosion process can be slowed by adding a thin layer of glass on top of the entire array. A sol-gel process can be used to deposit thick layer, on the order of about a 100 nm. A thinner crystalline layer of $SiO_2$, $Al_2O_3$ or $Y_2O_3$ works too, and may be deposited by atomic layer deposition or plasma assisted atomic layer deposition, optionally after array burn-in for uniform plasma.

A through-hole 118 helps reduce the array capacitance and is a ventilation hole for a fluid to flow from a drive electrode 110 to a ground electrode 108. Such fluids include oxygen, helium, nitrogen, sulfur hexafluoride, carbon dioxide, air, and other gases. In the preferred embodiment, the fluid is air at ambient pressure, about 1 atmosphere. The oxygen in the air is ionized by the plasma generated by the emitters 107, creating ozone. The through-holes 118 are made by drilling, etching, cutting, laser cutting, punching, or other method. In certain embodiments a through-hole is lined with a structure that directs the fluid to each electrode such as a pipe, tube, channel, or the like. A through-hole 118 can be circular, rectangular, triangular, trapezoidal, hexagonal, or other shape.

A drive electrode 110 is capacitively coupled to ground electrode 108 at a point or points where the ground electrode touches the drive electrode such that when a high-enough voltage is applied to a drive electrode 110, the surrounding fluid is ionized and a plasma is created, causing electrons to flow between the drive and ground electrode.

Figure 15A:
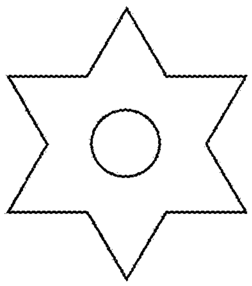
FIGS. 15A-D illustrate ground electrodes having points of various shapes.
Figure 15B:
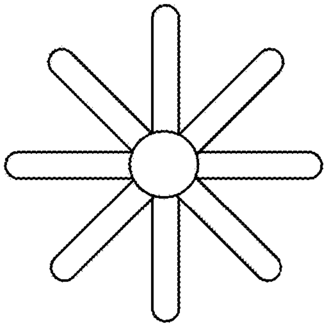
Figure 15C:
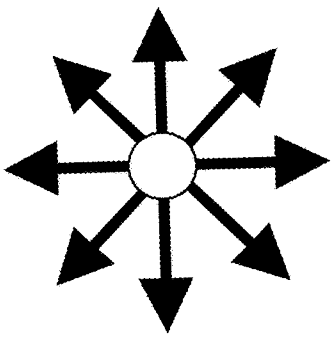
Figure 15D:
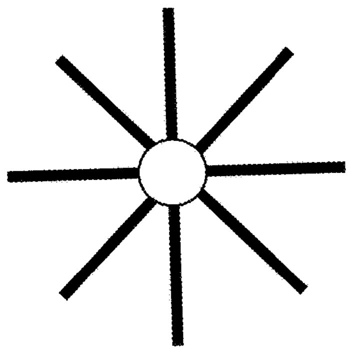

It is desirable to have a sharp point where the plasma is generated, since this is used to help initiate the plasma. The sharp points may take any form, such as a sharp point, a blunt point, a spear point a radius, or the like. FIG. 3 illustrates an embodiment in which the ground electrode 108 is a star with six sharp points 120. FIG. 4 illustrates an embodiment in which the ground electrode 108 is a triangle with three sharp points 120. FIG. 15A illustrates an electrode with six sharp points; FIG. 15B shows blunt points; FIG. 15C shows spear points; and FIG. 15D shows radius points.

A drive electrode 110, drive track 112, ground electrode 108 and a ground track 104 can be printed, etched, laminated, or otherwise disposed onto the substrate 102. They can be made of copper, silver, nickel, or any other conductive material. The can be insulated, such as by a solder mask, polyester film such as Mylar®, mica, polypropylene, polytetrafluoroethylene such as Teflon®, or the like, and in other embodiments are not insulated. For manufacturing convenience, preferably the drive electrode 110 and ground drive 112 are made of the same material and disposed onto the substrate 102 at the same time. Similarly, preferably the ground electrode 108 and ground track 104 are made of the same material and disposed onto the substrate 102 at the same time. Alternatively the drive electrode 110, drive track 112, ground electrode 108 and a ground track 104 are made of different materials and may be disposed on the substrate in processes occurring at the same or different times.

Figure 5:
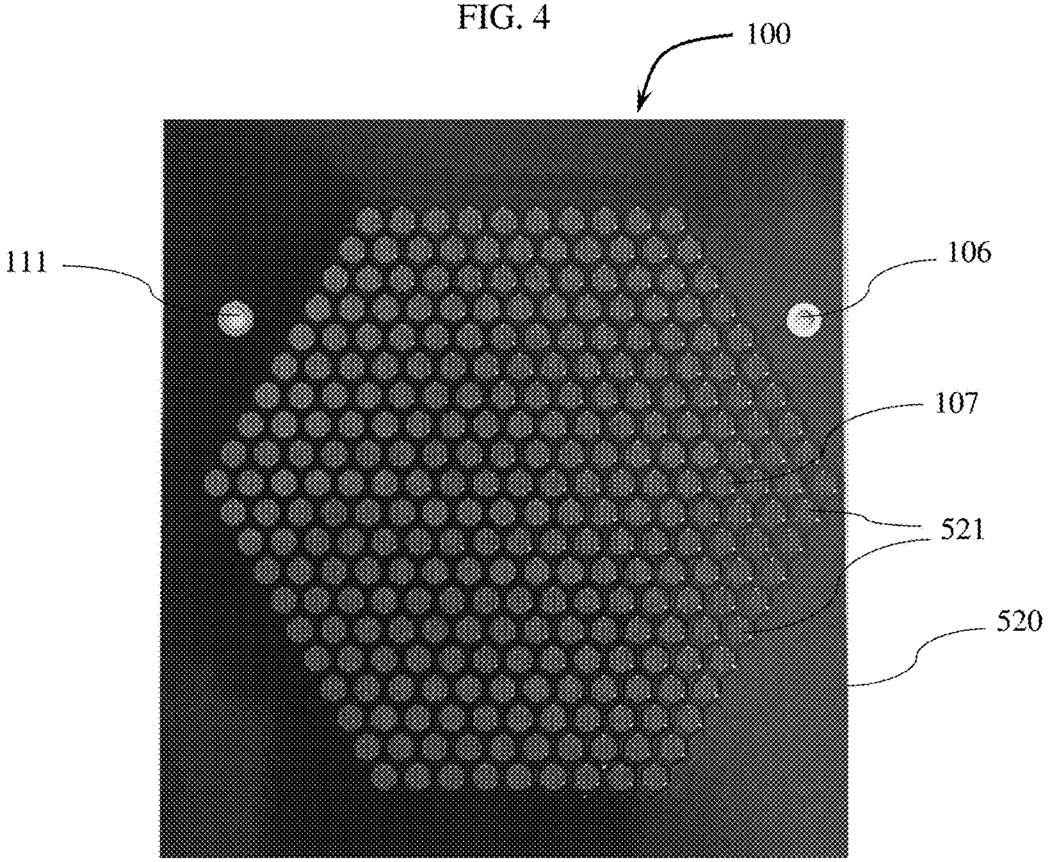
FIG. 5 is a top view of a fourth embodiment of a non-thermal device with a woven array of plasma emitters.
Figure 6:
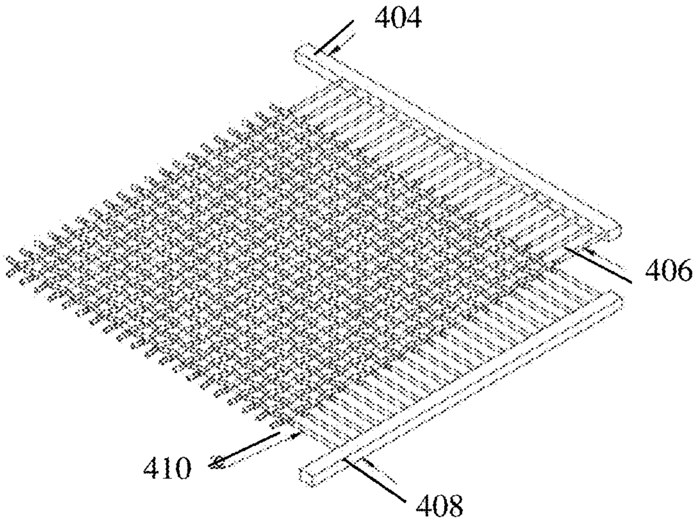
FIG. 6 is a schematic illustrating in perspective a portion of the woven array of FIG. 5.

FIGS. 5 and 6 show another embodiment of a non-thermal device 100 wherein a plurality of plasma emitters 107 is created at the intersections of wires that are woven together. The wires 410 of drive electrode 408 are woven with the wires 406 of ground electrode 404 to form a woven array. One electrode is connected to a plurality of insulated wires and the other connected to a plurality of uninsulated wires. If the wire insulation is a polymer, a coating, such as $SiO_2$, is preferred to prevent ashing. The air in the interstitial space between the wires is ignited to form a plasma. Wires can be copper, silver, nickel, or any other conductive material. The wires are insulated with non-conductive or dielectric materials such as plastic, rubber-like polymers, or varnish. In FIG. 5 the emitters 107 are covered by a rigid sheath 520 having hexagonal apertures 521.

The drive terminal 111 and ground terminal 106 are printed, cut, punched, laminated, etched, connected, or otherwise attached to the drive track 112 and ground track 104, respectively. There are at least those two terminals for each array of emitters, but there may be as many terminals as desired. For example, there may be two terminals for each emitter 107, or there may be more than two terminals for each emitter 107, for example if extra terminals are desired for redundancy in case of failure, or to have better placement for connection to the voltage source. Preferably the terminals 111 and 106 are attached to or integral with the substrate, such as with solder pads, banana plugs, ring terminals, spade terminals, pin terminals, or the like.

The emitters 107 can be arranged in a variety of relative positions, such as lines, concentric circles, random placement, etc. The arrangement of emitters is sometimes referred to herein as an array. An array can take on any shape to fit the user's needs. Typically the arrangement of the emitters 107 is generally symmetrical, such as a rectangle or hexagon, but the arrangement can be non-symmetrical too, which can be useful for using a single substrate target separate areas with different concentrations of plasma. FIG. 1 illustrates the emitters 107 arranged in rows, and each row is offset from the previous row. This same pattern is repeated with as many rows as the user needs to form the desired size of the array. The rows illustrated in FIG. 1 have 8 emitters each, but any number of emitters can be used in each row. The rows illustrated in FIG. 7 have 8 emitters each, but any number of emitters can be used in each row.

Figure 14:
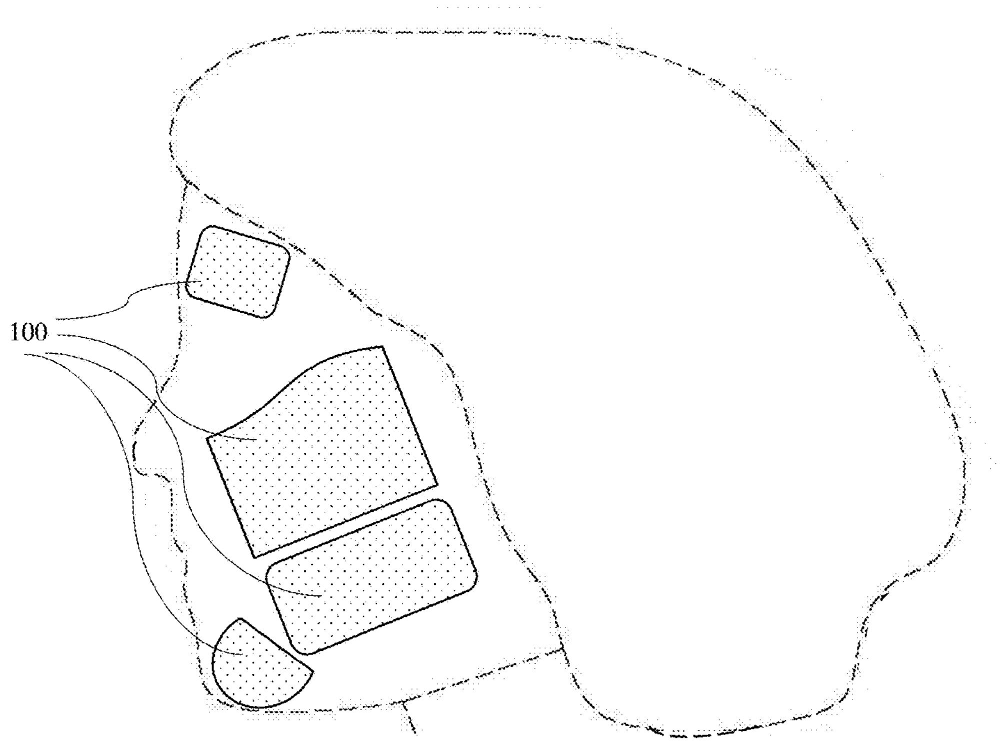
FIG. 14 illustrates plasma devices used to treat a patient's face in which several smaller devices are connected to each other to effectively create a larger area of plasma discharge.

The size of the array ranges from microscopic to macroscopic and, while theoretically unlimited, in practice is limited by manufacturing techniques. In practice, the arrays are typically less than 5 inches in any dimension. If a larger area of plasma discharge is desired, smaller arrays can be placed side-by-side and connected to each other to effectively create a larger array controlled as a single array. FIG. 14 illustrates plasma devices 100 used to treat a patient's face in which several smaller arrays are connected to each other to effectively create a larger area of plasma discharge. In other cases, the smaller arrays are placed sized-by-side to create a larger array, but are not connected to each other so that they can be controlled independently.

Plasmas can be defined in a number of characteristics including size typically in meters), lifetime (seconds), density (particles per cubic meter) and temperature. In certain embodiments a first emitter 107 has a different plasma strength than a second emitter 107. The plasma strength is determined by a number of factors including dielectric thickness, drive voltage (which determines the duty cycle in which the plasma is ignited and retained), and atmospheric pressure. Typically the resultant plasma is fan shaped, extending about 0.8 mm from the point and about 120 degrees of fan.

Figure 8:
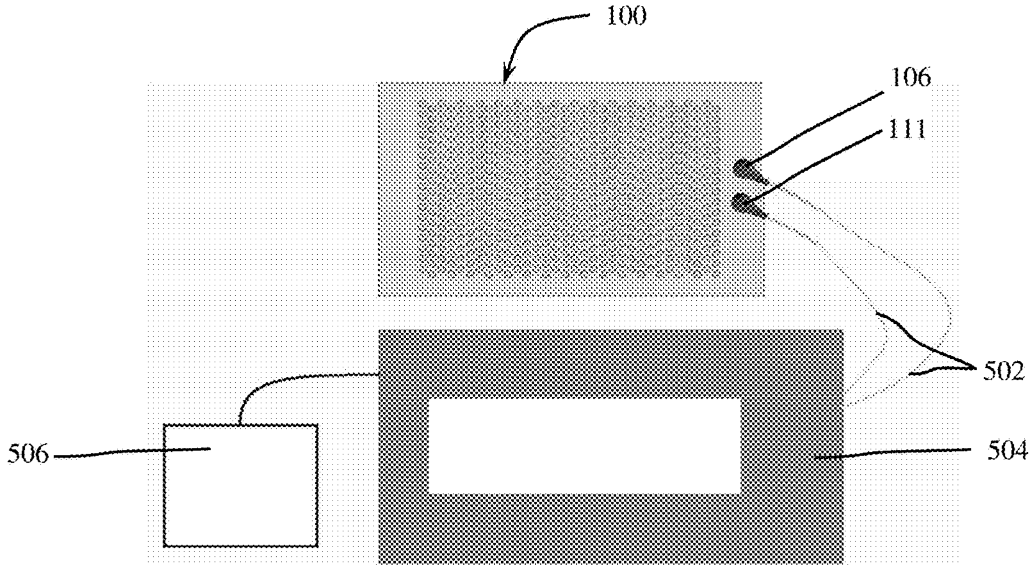
FIG. 8 illustrates a general overview of a non-thermal plasma device with a controller and a power supply.

To create the plasma, a voltage is applied to one or more drive electrodes 110 with an AC power supply 506. The array is driven by a high voltage transformer, designed to resonate with the array capacitance. In a preferred embodiment, the power supply is a resonant transformer, with a half bridge driver on the transformer primary. The transformer primary bias is derived from a boost converter, which is connected to a rechargeable battery pack, charged by a cell phone charger connected to mains power, a cell phone, or a vehicle power outlet. See FIG. 8A. The characteristics of the power supply will depend on the size of the array. The inductance of the transformer's secondary winding and the capacitance of the array of emitters forms a parallel LC circuit with a particular resonant frequency.

Preferably the voltage is controlled wirelessly or with wires by a controller 504. If using a wired controller, the controller 504 is connected to the device 100 by leads 502. See FIG. 8. The smart phone may also act as a programmable controller using a downloaded mobile application. In other embodiments the controller may be a customized control box, a desktop computer, a laptop, or the like. The controller can drive the transformer at its resonant frequency for the sake of power efficiency. If a therapeutic plasma frequency is found, the plasma frequency can be adjusted by adding parallel capacitance of an appropriate value. The AC drive voltage can also be modulated if a therapeutic modulation frequency is found. In an alternative embodiment, the transformer driver can be configured as an oscillator, so the transformer operates at the resonant frequency by default. In this case, a signal from the transformer driver is sent to the controller to synchronize the measurement of voltages and currents. This is can be used for accurate power measurement, for instance.

The controller controls aspects that control the functionality of the device 100 such as time on/off, strength of plasma, strength of a plasma field from electrode to electrode, frequency, power, and the like. In certain embodiments the AC voltage is applied to the drive electrodes is on-off modulated in pulses, typically at a frequency between above 0 Hz to about 10 kHz. Alternatively a continuous wave voltage is applied to the drive electrodes. With the drive electrodes 110 at a high potential relative to the ground electrode 108, current flows through the drive electrodes 110 and through a fluid in the through-hole 118 and around the array. The fluid is ionized to create a plasma region around each drive electrode 110, ground electrode 108 or both. The ions from the ionized fluid pass a charge to a plurality of ground electrodes 108 or to an area of lower potential.

Figure 7:
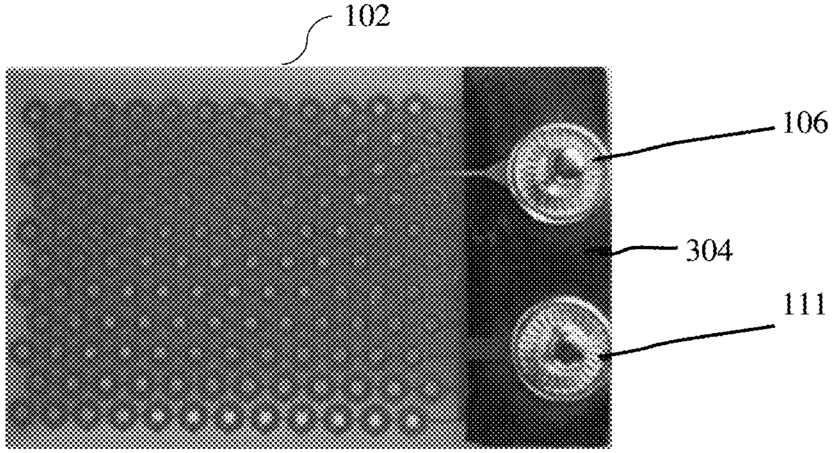
FIG. 7 is a photograph of the first embodiment of the device on a flexible substrate and its terminal connection points.

FIG. 7 shows a non-thermal plasma device in which an insulative layer 304 is attached to the substrate 102, under the ground terminal 106 and driver terminal 111. The insulative layer 304 can be neoprene, polymer coating, Mylar®, Teflon®, or the like.

Figure 9:
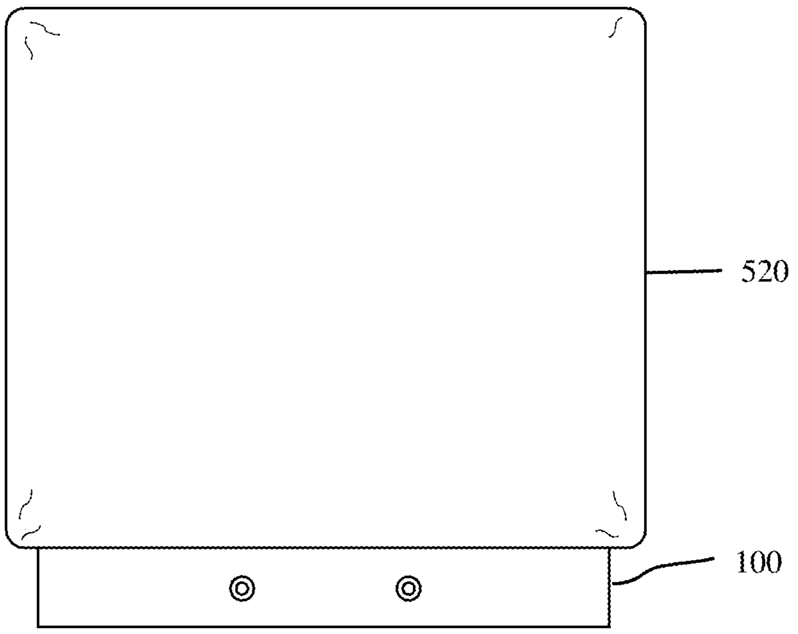
FIG. 9 is a top view of a non-thermal plasma device that is partially covered with a flexible sheath.
Figure 10:
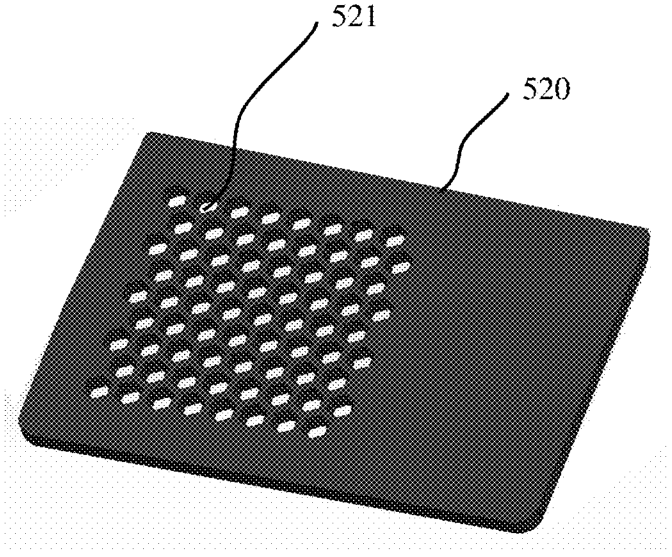
FIG. 10 is a top perspective view of rigid sheath partially covering a non-thermal plasma device.

FIG. 9 shows a non-thermal plasma device 100 with a sheath 520 covering at the plasma emitters. In some embodiments only some of the emitters are covered. In a preferred embodiment the sheath 520 is an electrical insulator that acts as a barrier between the device and a surface of interest. The electrical insulator 520 allows plasma generated from the device to effect and react with a surface of interest, but does not allow fluids to permeate thru the cover to the created plasma, and surface of a substrate. Thus it protects a user or surface from possible electrical shocks and prevents liquids from getting to the electrodes that might cause electrical shorts. Preferably the sheath 520 is flexible and made of PTFE, which provides a water-resistant yet breathable covering. Flexible sheaths can also be made of neoprene, hydrophobic polyester, hydrophilic polyether, or the like. FIG. 10 shows one embodiment of a rigid sheath 520 with apertures 521 centered on the through-holes 118 that are on the non-thermal plasma device. The sheath 520 can vary in length, width, and height to fit a non-thermal plasma device's size and shape.

Figure 11:
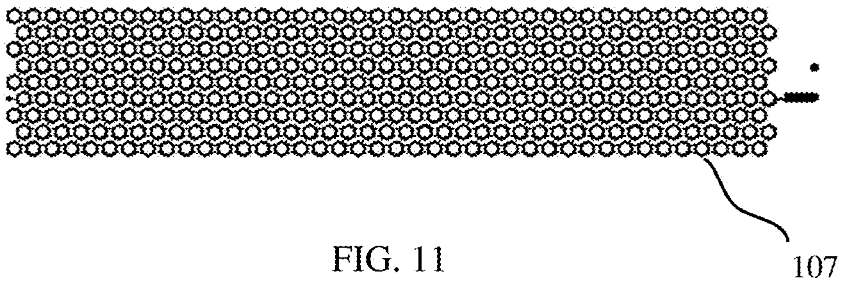
FIG. 11 is a top view of a fifth embodiment of a non-thermal plasma device of the present invention in which the plasma emitters are in a rectangular array.
Figure 12:
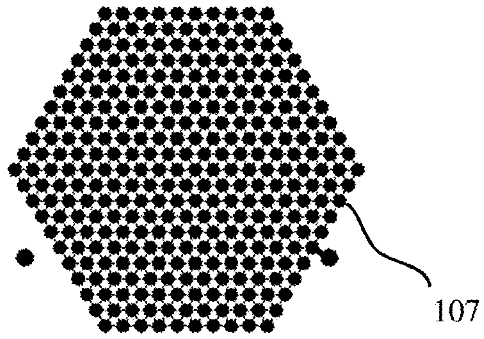
FIG. 12 is a top view of a sixth embodiment of a non-thermal plasma device of the present invention in which the plasma emitters are in a hexagonal array.
Figure 13:
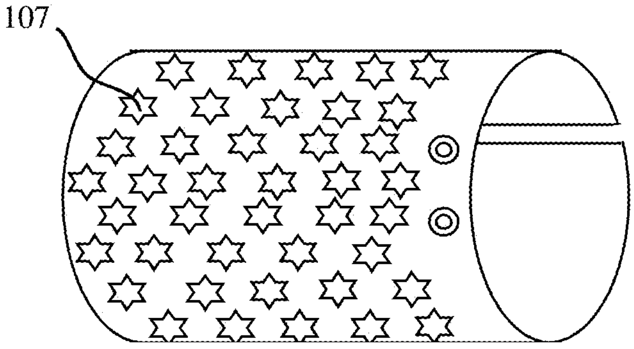
FIG. 13 is a perspective view of a seventh embodiment illustrating a non-thermal plasma device as a tube.

A non-thermal plasma device can conform to any shape or size, including human body parts. FIGS. 11, 12 and 13 show examples of additional embodiments of the device 100. FIG. 11 shows a rectangular array of plasma emitters 107 in which one side of the array is substantially longer than the other side. This arrangement may be particularly useful for the treatment of large narrow surface areas. FIG. 12 shows a hexagonal array of plasma emitters 107. FIG. 13 shows a device 100 formed into a tube, with plasma emitters arranged along the surface of the tube. This arrangement may be particularly useful for the treatment of tubular-shaped areas such as fingers so that the inside of the tube stays in contact with the outside of the finger. This arrangement may also be particularly useful for threating the inside surface of a tubular human body part such as an ear canal in which the outside of the tube stays in contact with the inner surface of the ear canal. The tubular device can be preformed on a rigid or flexible substrate. Alternatively, a rectangular device on a flexible substrate can be bent into a tube at the time of treatment.

Plasma devices of the present invention can be used for treating many types of surfaces for purposes including cleaning, decontaminating, sterilization, and healing. For example:

Example 1

Decontamination of a Cell Phone

Individuals take cell phones where everywhere they go and are constantly using it after using the restroom, touching dirty door knobs, shaking others' hands, sharing the phone with others, and touching money. All these items are full of bacteria, which can spread to the individual's cell phone. Consequently, cell phones have up to 18 times more bacteria than a public restroom. In certain embodiments a non-thermal plasma device can be placed around a cell phone. Once the non-thermal device is turned on the bacteria on the phone will be killed, in effect sanitizing the cell phone from any harmful bacteria.

Example 2

Biological Warfare Decontamination Suit

In war biological weapons are used to kill and hurt soldiers. In certain embodiments a biological warfare suit can be lined with non-thermal plasma devices. When a soldier has been contaminated with a biological weapon, the soldier can put on the non-thermal-plasma lined suit. Once the suit is on, the non-thermal plasma devices are turned on and the soldier can be decontaminated. The suit is reusable.

Example 3

Killing Fungus or Bacteria with a Non-Thermal Plasma Device

A voltage supplied to a plasma device can be modulated (pulsed or keyed on and off) at a rate of about 1 Hz to about 10 kHz. Specific modulation frequencies (the so-called Rife frequencies) have therapeutic effects in which a specific frequency is correlated to kill a specific microorganisms, including forms of bacteria, virus, fungus, mold, etc. The controller can use these frequencies to produce biological effects beyond those produced by reactive oxygen species. The resulting biological effects created by a non-thermal plasma device over a large surface area can eliminate microorganisms on any surface type.

Example 4

Method for Creating Ozone

Ozone is an unstable, but highly beneficial molecule, and is created by plasma. Plasma is a mixture of neutral and charged particles. When a voltage is applied to an array of plasma emitters 107 that are in a gas containing oxygen, the plasma emitters generate a transfer of electrons that generates ozone. Ozone can be applied to a human body for therapeutic effects, to water for oxidizing pathogens and synthetics residues in the body, and to olive oil for ingesting which gives an individual a steady internal application of ozone. In addition, ozone can be used as an air disinfectant killing germs, infectious microorganisms, and neutralizing many biological problems like bacteria, viruses, mold and chemical outgassing.

Example 5

Cosmetic Treatments

Nitric oxide is a free-radical that has been shown to be beneficial in treating photodamaged facial skin by burning the old damaged skin cells so they can be sloughed off and replaced with new, healthy skin cells. An array of plasma emitters that are in a gas containing nitrogen are placed on the desired treatment area of the skin and the plasma emitters generate nitric oxide across the entire treatment area. In this was treatment using the present device is much faster than the conventional method of treating the area with plasma plume that is repeatedly passed, or scanned, across the treatment area.

While there has been illustrated and described what is at present considered to be the preferred embodiments of the present invention, it will be understood by those skilled in the art that various changes and modifications may be made and equivalents may be substituted for elements thereof without departing from the true scope of the invention. The embodiments of the invention described herein are not intended to be exhaustive or to limit the invention to precise forms disclosed. Rather, the embodiments selected for description have been chosen to enable one skilled in the art to practice the invention. Therefore, it is intended that this invention not be limited to the particular embodiments disclosed, but that the invention includes all embodiments falling within the scope of the appended claims.

We claim:

1. A non-thermal plasma device comprising:

a. a substrate having a top surface and a bottom surface, the substrate having no through-holes between the top and bottom surfaces, the substrate made of a dielectric material;

b. a plurality of drive electrodes on the top surface of the substrate; and c. a plurality of ground electrodes on the bottom surface of the substrate, such that a plurality of plasma emitters are formed on the surface of the substrate between the drive electrodes and the ground electrodes.

2. The device according to claim 1 wherein the substrate is flexible.

3. The device according to claim 2 wherein the substrate is made of FR-4.

4. The device according to claim 1 wherein each drive electrode and ground electrode are centered over each other.

5. The device according to claim 1 further comprising:

a. a conductive drive track on the top surface of the substrate connected to each drive electrode; and b. a conductive ground track on the bottom surface of the substrate connected to each ground electrode.

6. The device according to claim 5 further comprising a drive terminal connected to the drive track and a ground terminal connected to the ground track.

7. The device according to claim 6 further comprising a voltage source connected to the drive terminal.

8. The device according to claim 7 wherein the voltage source is a cell phone.

9. The device according to claim 1 further comprising an insulative sheath covering at least a portion of the plasma emitters.

10. The device according to claim 1 wherein the plasma emitters are aligned in rows that are offset from the previous row.

11. The non-thermal plasma device of claim 1 wherein each of the ground electrodes comprises a sharp point.

12. A non-thermal plasma device comprising:

a. a voltage source;

b. a plurality of plasma emitters connected to one another to form an array such that, when the array is connected to the voltage source, a plurality of corona discharges is emitted from the plasma emitters; and c. a removable insulative sheath covering at least a portion of the plasma emitters.

13. The device according to claim 12 wherein the plasma emitters are formed in a flexible substrate.

14. The device according to claim 12 wherein the rigid substrate conforms to the shape of a human body part.

15. The device according to claim 12 wherein the plasma emitters are formed in a substrate that has the shape of a tube.

16. The device according to claim 12 wherein the sheath is removable.

17. A non-thermal plasma device comprising:

a. a substrate having a top surface and a bottom surface, the substrate made of a dielectric material;

b. a plurality of drive electrodes on the top surface of the substrate;

c. a plurality of ground electrodes on the bottom surface of the substrate, with each ground electrode comprising a sharp point; and d. a plurality of through-holes in the substrate, wherein the drive electrodes and the ground electrodes are centered over the through-holes on the surface of the substrate such that a plurality of plasma emitters are formed in the substrate between the drive electrodes and the ground electrodes.

18. The device according to claim 17 further comprising:

a. a conductive drive track on the top surface of the substrate connected to each drive electrode;

b. a conductive ground track on the bottom surface of the substrate connected to each ground electrode;

c. a drive terminal connected to the drive track and a ground terminal connected to the ground track; and d. a voltage source connected to the drive terminal.

19. The device according to claim 18 wherein the voltage source is a cell phone.

20. The device according to claim 17 further comprising a sheath made of PTFE covering at least a portion of the plasma emitters.

* * * * *